United States Patent [19]

Kawai et al.

[11] Patent Number: 5,387,516
[45] Date of Patent: Feb. 7, 1995

[54] HEAT STABLE DEBRANCHING ENZYME FROM A BACILLUS MICROORGANISM

[75] Inventors: Michiyo Kawai; Shigeharu Mori; Susumu Hirose; Hiroji Tsuji, all of Aichi, Japan

[73] Assignee: Amano Pharmaceutical Co., Ltd., Aichi, Japan

[21] Appl. No.: 22,163

[22] Filed: Feb. 25, 1993

[30] Foreign Application Priority Data

Feb. 26, 1992 [JP] Japan .................. 4-076181

[51] Int. Cl.$^6$ .................. C12N 9/44; C12N 1/20; C12N 1/00; C12P 19/16
[52] U.S. Cl. .................. 435/210; 435/98; 435/252.5; 435/832
[58] Field of Search .................. 435/210, 252.5, 832, 435/98

[56] References Cited

U.S. PATENT DOCUMENTS

| | | | |
|---|---|---|---|
| 3,804,715 | 4/1974 | Sugimoto et al. | 435/95 |
| 3,862,005 | 1/1975 | Miyake et al. | 435/137 |
| 3,992,261 | 11/1976 | Takasaki et al. | 435/98 |
| 4,011,139 | 3/1977 | Horwath et al. | 435/210 |
| 4,902,622 | 2/1990 | Nakai et al. | 435/210 |

*Primary Examiner*—David M. Naff
*Assistant Examiner*—Mike Meller
*Attorney, Agent, or Firm*—Sughrue, Mion, Zinn, Macpeak & Seas

[57] ABSTRACT

A debranching enzyme, a process for producing the enzyme, a microorganism capable of producing the enzyme, and a process for producing glucose liquids using the enzyme are disclosed. The microorganism is preferably Bacillus FERM BP-4204, the enzyme is a debranching enzyme which acts on alpha-1,6 glucosidase bonds on produce straight chain amylose, acts on pullulan and also acts on relatively long chain saccharides, wherein said substrate specificity for activity on pullulan is set at 100, the activity of said enzyme on soluble starches relative to said activity on pullulan is from about 20 to 40, the activity of said enzyme on glycogen relative to said activity on pullulan is from about 30 to 60, and the activity of said enzyme on amylopectin relative to said activity on pullulan is from about 10 to 30, has an optimum pH from about 4.5 to 6.0, an optimum temperature from about 60° C. to about 70° C., a molecular weight of about 98 kD as measured by SDS-PAGE, and an isoelectric point of about 2.9. The enzyme can be also used for the production of glucose and maltose.

2 Claims, 2 Drawing Sheets

HEAT STABLE DEBRANCHING ENZYME FROM A BACILLUS MICROORGANISM

FIELD OF THE INVENTION

This invention relates to a substantially pure α-1,6-glucosidase, a biologically pure culture of a microorganism belonging to the genus Bacillus and capable of producing this enzyme, a process for producing this enzyme from a culture of the microorganism, and a process for producing glucose, maltose, etc. using the enzyme. More particularly, this invention relates to a substantially pure culture of Bacillus sp. APC-9603 newly isolated from soil, a debranching enzyme, a process for producing the enzyme, and a process for producing glucose, maltose, etc. using the enzyme.

BACKGROUND OF THE INVENTION

α-1,6-Glucosidases are enzymes which cleave the α-1,6-glucoside bond in starch etc. to produce straight chain amyloses. They are classified by substrate specificity primarily into isoamylase (EC 3.2.1.68) and pullulanase (EC 3.2.1.41), etc. Pullulanase is widely employed in combination with endo-type amylases and exo-type amylases in the production of malto-oligosaccharides, such as glucose, maltose, maltotriose, maltotetraose, maltopentaose, maltohexaose, etc.

While α-1,6-glucosidase-producing microorganisms have been previously found amongst yeast, various bacteria have recently been reported to be capable of producing an α-1,6-glucosidase. Bacteria capable of producing an α-1,6-glucosidase which have been reported thus far include, for example, *Aerobacter aerogenes, Escherichia intermedia, Pseudomonas amyloderamosa, Streptococcus mitis,* and genera *Cytophaga, Streptomyces* and *Flavochromogenes.*

Microorganisms belonging to the genus Bacillus and capable of producing an α-1,6-glucosidase include *Bacillus cereus* IFO 3001, *Bacillus fermus* IFO 3330, *Bacillus acidopullulyticus,* and *Bacillus sectorramus.*

The optimum pH of most of the known α-1,6-glucosidases is in a neutral to weakly alkaline region. Therefore, disadvantages arise in the field of saccharification where reactions are conducted in an acidic region.

On the other hand, α-1,6-glucosidases having their optimum pH in an acidic region thus far reported include those produced by *Pseudomonas amyloderamosa, Bacillus acidopullulyticus,* and *Bacillus sectorramus.* However, the enzymes produced from the first two of these microorganisms are not heat resistant, which is industrially disadvantageous, or a long cultivation time is required for these bacteria to obtain a substantial amount of the desired enzyme, which is economically disadvantageous. *Bacillus sectorramus* and the α-1,6-glucosidase produced therefrom were reported as being free from these disadvantages. However, development of an α-1,6-glucosidase with industrially advantageous properties is still required.

SUMMARY OF THE INVENTION

An object of the present invention is to provide a substantially pure α-1,6-glucosidase with industrially advantageous properties, i.e., an optimum pH in an acidic region for saccharification with higher heat resistance than ever and with other industrially advantageous properties.

Another object of the present invention is to provide a biologically pure culture of a microorganism capable of producing an α-1,6-glucosidase having industrially advantageous properties.

A further object of the present invention is to provide a process for producing such an α-1,6-glucosidase using such a microorganism.

A still further object of the present invention is to provide a process for producing glucose or maltose using such an enzyme.

In pursuit of a microorganism capable of producing a considerable amount of a novel α-1,6-glucosidase having an optimum pH in an acidic region suitable for saccharification, with higher heat resistance than conventional α-1,6-glucosidases and, in addition, with other industrially advantageous properties, screenings using various kinds of soil collected have been conducted. As a result, they have found a new microorganism strain which was isolated from the soil of Aichi Prefecture, Japan and identified as belonging to the genus Bacillus which is capable of producing a large quantity of an α-1,6-glucosidase. On examination, it was found that the enzyme produced by this strain possesses industrially useful activity that has not been observed in the conventional α-1,6-glucosidases, i.e., broad substrate specificity. The present invention has been completed based on these findings.

The present invention provides a substantially pure novel debranching enzyme which has heat resistance, an optimum pH in an acidic region, and broad substrate specificity.

The present invention also provides a biologically pure culture of novel strain, Bacillus sp. APC-9603, capable of producing the above-mentioned novel debranching enzyme in a large quantity.

The present invention further provides a process for producing the above-mentioned enzyme comprising cultivating Bacillus sp. APC-9603 and recovering the desired enzyme from the culture.

The present invention still further provides a process for producing glucose by using the above-mentioned enzyme.

The present invention yet further provides a process for producing maltose by using the above-mentioned enzyme.

DETAILED DESCRIPTION OF THE INVENTION

Figure 1:
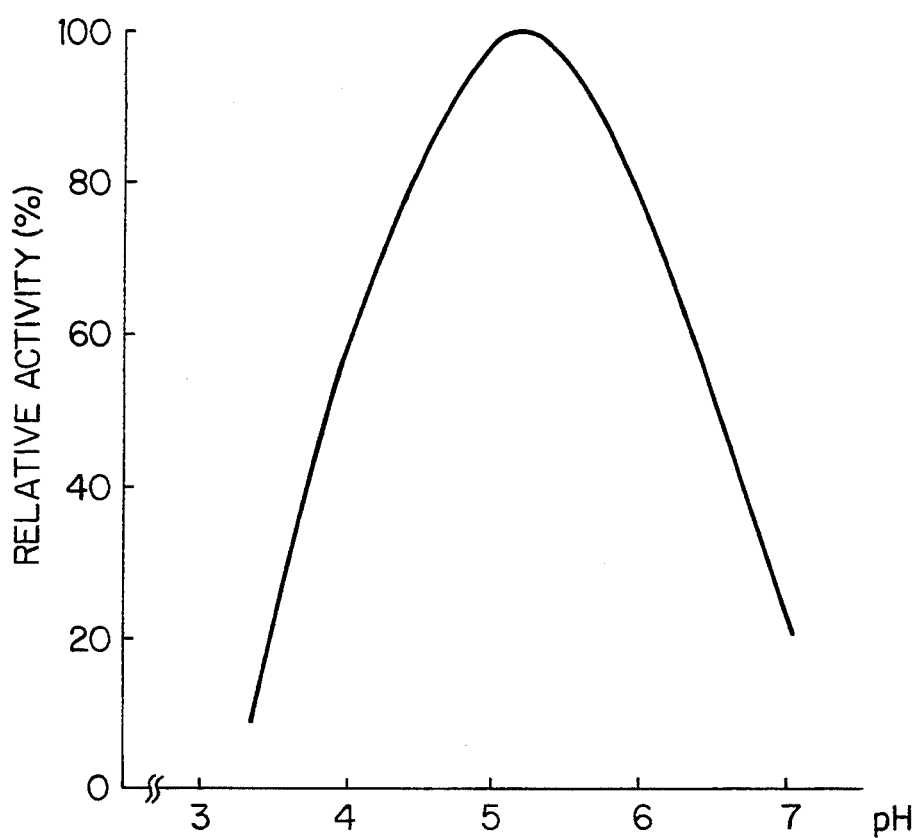
FIG. 1 is a graph showing the optimum pH of the debranching enzyme according to the present invention.

Microorganisms capable of producing a novel debranching enzyme having heat resistance, an optimum pH in an acidic region, and broad substrate specificity include Bacillus sp. APC-9603 isolated from the soil of Aichi Prefecture, Japan.

Bacillus sp. APC-9603 has the following characteristics and properties. Bacillus sp. APC-9603 has been deposited since Feb. 5, 1992 with National Institute of Bioscience and Human-Technology, Agency of Industrial Science & Technology, MITI, 1-3, Higashi 1-chome, Tsukubashi, Ibaraki-ken 305, Japan and has received accession number FERM P-12746 (FERM BP-4204 under the Budapest Treaty).

A. Morphological Characteristics
1) Shape: Bacillary
2) Size: 0.5 to 0.8 × to 4.0 μm
3) Motility: positive
4) Sporangium: circularly swollen (1.0 to 1.5 μm)
5) Location of Spores: edges or nearly edges of cells
6) Properties of Colony: semitransparent, circular protrusion with glossy surface, yellow-tinted surface growth
7) Gram stain: changeable (positive with juvenile cells; unsettled with aged cultures)

B. Growth Conditions and Physiological Properties
1) Growth in Nutrient Bouillon: negative
2) Aerobic Growth: positive
3) Anaerobic Growth: negative
4) Growable temperature: 13° to 45° C.
5) Optimum growth temperature: 33° to 38° C.
6) Growable pH: 4.0 to 6.0
7) Optimum Growth pH: 4.5 to 5.5
8) Tolerance to NaCl: 0 to 5.0%
9) Nitrate Reduction: positive
10) Pigment Production: negative
11) Utilization of Citric Acid: negative
12) Utilization of Propionate: negative
13) Catalase Activity: negative
14) Tyrosine Decomposition: negative
15) Starch Hydrolysis: negative
16) VP Test: negative
17) Lecithinase: negative
18) Indole Production: negative
19) Esculin Decomposition: positive
20) Litmus Milk Reaction: unchanged (30 days)
21) Gelatin Decomposition: positive (weak)
22) Casein Decomposition: negative
23) Deamination Reaction of Phenylalanine: negative
24) pH of VP Broth: 5.0
25) Utilization of Sugars:
   Production of acid from glucose: positive (delayed)
   Production of acid from mannitol: positive
   Production of acid from arabinose: positive
   Production of acid from xylose: positive
   Production of acid from sucrose: positive (delayed)
   Production of acid from lactose: positive (delayed)
   Production of acid from trehalose: positive
   Production of gas from mannitol: negative Of the above-identified tests, those for Gram stain, catalase, morphology, and the like were conducted on a yeast extract-inorganic acid medium as specified; the growth tests (pH, temperature, etc.) were conducted on a Trypticase Soy Agar medium (produced by BBL); and the other physiological tests were conducted on the 14-day culture at a pH of 5.0±0.1.

The identification of the strain was made based on the above microbial properties according to "Bergey's Manual of Determinative Bacteriology" (8th Ed.), "The Genus Bacillus", and Ruth B. Gordon, *Agricultural Handbook*, No. 427, Agriculture Research Service, U.S. Department of Agriculture, Washington D.C. (1973).

That is, the strain belongs to genus Bacillus from the positive Gram stain, presence of spores, aerobic growth, and so forth. The strain is very similar to *Bacillus circulans* but is different therefrom in terms of negative catalase activity. Species belonging to the genus Bacillus with negative catalase activity include *Bacillus larvae*, *Bacillus popilliae*, and *Bacillus lentimorbus*, and the strain of the present invention is obviously different from all of these species. Accordingly, the strain was designated Bacillus sp. APC-9603.

Bacillus sp. APC-9603 is distinctly distinguished from the known debranching enzyme-producing microorganisms, *Bacillus acidopullulyticus* and *Bacillus sectorramus*, as summarized in Table 1 below.

TABLE 1

|  | Bacillus sp. APC-9603 | B. sectorramus | B. acidopullulyticus |
| --- | --- | --- | --- |
| Oxygen Demand | aerobic | facultative aerobic | aerobic |
| NaCl Tolerance | growable in 3.5% NaCl | growable in 3.5% NaCl | ungrowable in 3.5% NaCl |
| Catalase | negative | positive | positive |
| Decomposition of Tyrosine | negative | positive | negative |
| Citric Acid Utilization | negative | positive | negative |
| Acid Production from Mannitol | positive | negative | positive |
| VP Reaction | negative | negative | changeable |
| Casein Decomposition | negative | negative | changeable |
| Acid Production from Xylose or Arabinose | positive | positive | changeable |
| Thickness of Trophocyte | 0.6–3.5 μm | 1.0–1.3 μm | 0.6–1.0 μm |

The debranching enzyme according to the present invention can be obtained by inoculating Bacillus sp. APC-9603 to a culture medium and culturing such in a usual manner.

Suitable medium to be used contains adequate amounts of appropriate assimilable nitrogen sources, carbon sources, etc. Examples of typical nitrogen sources include organic substances commonly used for cultivation of microorganisms, such as meat extract, peptone, and corn steep liquor, and inorganic substances, such as ammonium chloride and ammonium sulfate. Examples of appropriate carbon sources include starch, liquefied starch, dextrin, maltose, glucose, and sucrose. Supplementary medium components include various metal salts, such as phosphates, magnesium salts, calcium salts, and manganese salts. If desired, the culture medium may contain minor organic or inorganic nutrient sources.

Cultivation can be carried out by inoculating the above-mentioned medium adjusted to pH 4.0 to 7.0 with Bacillus sp. APC-9603, and incubation at a temperature of 20° to 45° C. for 1 to 2 days using stationary culture, shake culture, or spinner culture with aeration. Cultivation is preferably carried out at 30° to 37° C. for 40 to 48 hours using spinner culture with aeration.

Recovery of the debranching enzyme produced from the culture and purification of the recovered enzyme can be performed by general enzyme recovery and purification methods. That is, microbial cells are removed from the culture by centrifugal separation or filtration to obtain a crude enzyme liquid. If desired, this crude enzyme liquid is then subjected to purification, such as salting out, precipitation, ultrafiltration, and various chromatographic techniques, to obtain a purified enzyme.

In greater detail, after completion of the cultivation, microbial cells were removed from the culture, and the supernatant liquor was concentrated to obtain a crude enzyme preparation having a high α-1,6-glucosidase unit activity. The crude enzyme preparation was subjected to ammonium sulfate fractionation, and further purified by affinity chromatography using γ-cyclodextrin-Sepharose 6B and SDS-polyacrylamide gel electrophoresis (hereinafter abbreviated as SDS-PAGE) to a single band.

The thus obtained novel debranching enzyme according to the present invention has the following enzymological and chemical properties.

1. Activity

The enzyme acts on α-1,6-glucoside bonds to produce straight chain amylose.

2. Substrate Specificity

When the activity of the present enzyme on pullulan is taken as 100, the relative activities on soluble starches, glycogens, and amylopectins are:

Soluble starches: 20 or more (usually, from 20 to 40),
Glycogens: 30 or more (usually, from 30 to 60),
Amylopectins: 10 or more (usually, from 10 to 30).

The activity of the enzyme on various origin polysaccharide substrates (1% in 100 mM McIlvaine's buffer solution, pH=5.0) is shown in Table 2 below, expressed relatively to activity on pullulan.

TABLE 2

| Polysaccharide (Source of Supply) | Relative Activity |
|---|---|
| Pullulan (Hayashibara Biochemical Laboratories) | 100 |
| Soluble Starch (Merck) | 32.6 |
| Soluble Starch (Katayama Chemical Industries) | 35.4 |
| Glycogen (oyster) | 16.7 |
| Amylopectin (corn) | 48.1 |
| Amylopectin (potato) | 41.0 |

3. Optimum pH

From about 4.5 to about 6.0 (around 5.2) (in 100 mM McIlvaine's buffer solution). FIG. 1 shows a plot of relative activity vs. pH.

4. Stable pH Range

Figure 2:
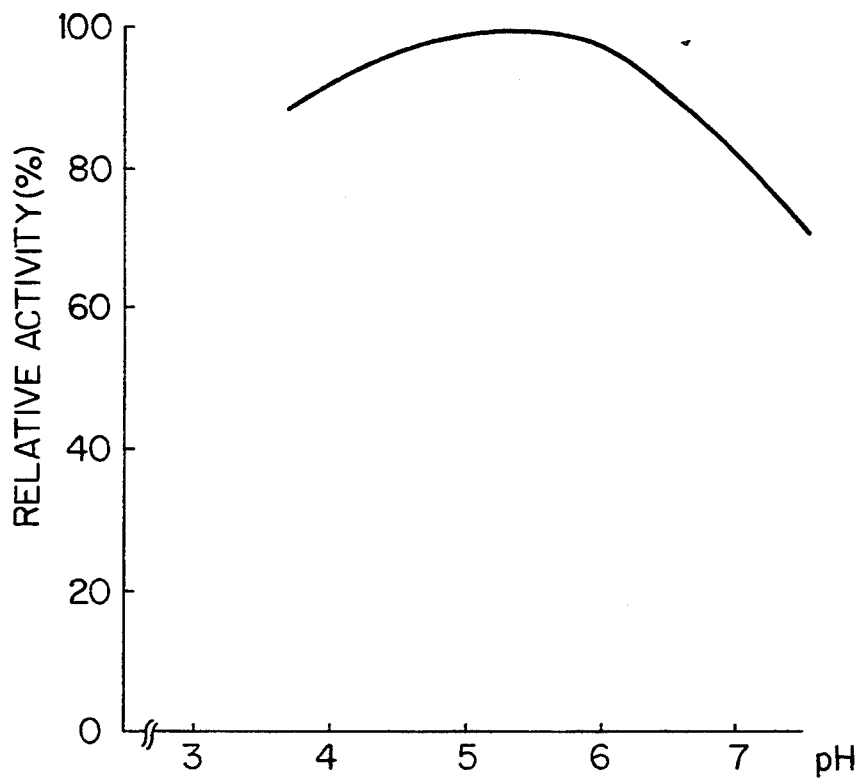
FIG. 2 is a graph showing the pH stability of the debranching enzyme according to the present invention.

Stable at pH of from 4.0 to 6.0 when treated at 40° C. for 30 minutes in 100 mM McIlvaine's buffer solution. A plot of pH vs. relative activity is shown in FIG. 2.

5. Optimum Temperature

Figure 3:
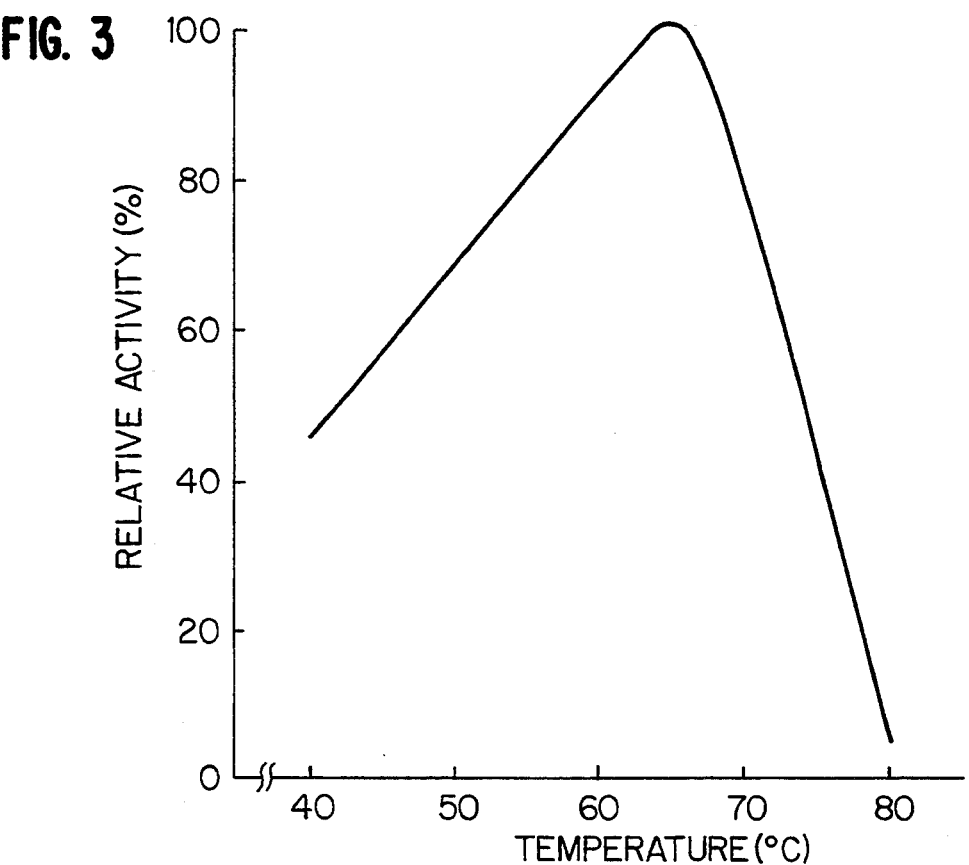
FIG. 3 is a graph showing the optimum temperature of the debranching enzyme according to the present invention.

From about 60° C. to about 70° C. (around 65° C.) (pH=5.0, 30-minutes reaction). A plot of temperature vs. relative activity is shown in FIG. 3.

6. Range of Temperature Appropriate for Activity

Figure 4:
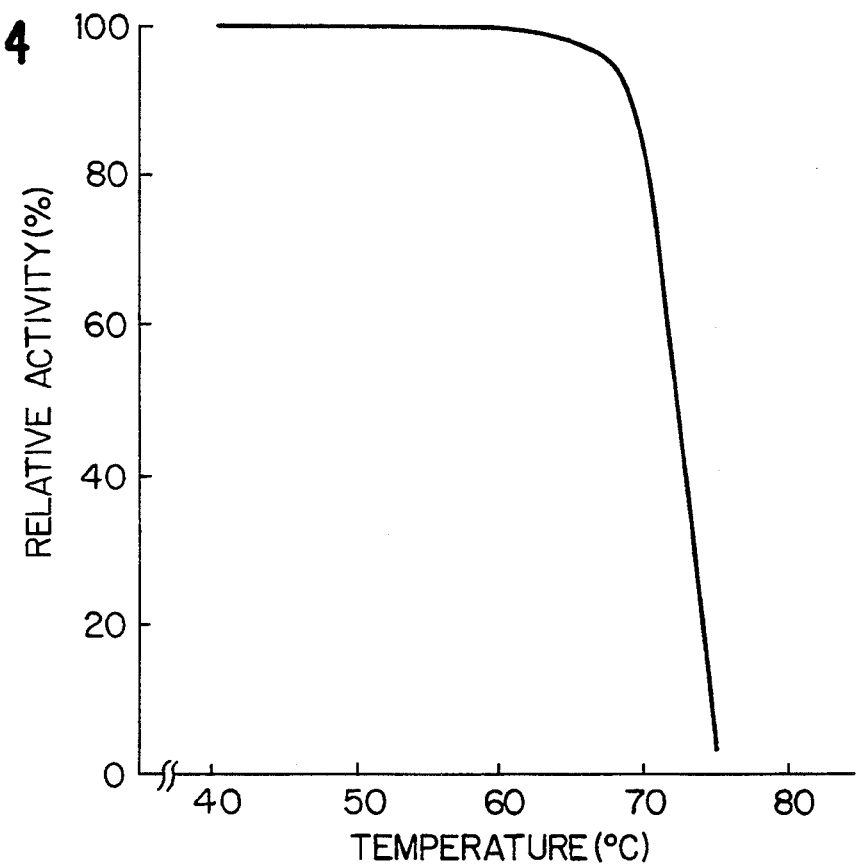
FIG. 4 is a graph showing temperature stability of the debranching enzyme according to the present invention.

80% stable when treated at 70° C. for 30 minutes. A plot of temperature vs. relative activity is shown in FIG. 4.

7. Inhibition

Slightly inhibited by p-mercuri-benzoic acid (hereinafter abbreviated as p-CMB) and EDTA. Non-inhibited by N-ethylmaleimide (hereinafter abbreviated as N-EMI) and monoiodoacetic acid (hereinafter abbreviated as MIA). The residual activity when treated with each of these inhibitors at a final concentration of 1 mM in a 50 mM acetic acid buffer solution (pH=5.0) at 40° C. for 30 minutes is shown in Table 3 below.

TABLE 3

| Inhibitor | Residual Activity (%) |
|---|---|
| none | 100 |
| EDTA | 90 |
| p-CMB | 81 |
| N-EMI | 104 |
| MIA | 105 |

8. Influence of Metal Salt

Substantially unaffected by $Mg^{2+}$, $Co^{2+}$, $Ca^{2+}$, $Ni^{2+}$, $Ba^{2+}$, $Cu^{2+}$, $Zn^{2+}$, and $Ag^{3+}$. Slightly inhibited by $Mn^{2+}$, $Fe^{3+}$, $Sn^{2+}$, and $Cd^{2+}$, and strongly inhibited by $Hg^{2+}$. The residual activity when treated with a metal salt at a final concentration of 1 mM per 14 u/ml of activity in a 50 mM acetic acid buffer solution (pH=5.0) at 40° C. for 30 minutes is shown in Table 4 below.

TABLE 4

| Metal Salt | Residual Activity (%) |
|---|---|
| None | 100 |
| $MgCl_2$ | 103 |
| $MnCl_2$ | 84 |
| $CoCl_2$ | 107 |
| $CaCl_2$ | 100 |
| $NiCl_2$ | 100 |
| $BaCl_2$ | 97 |
| $FeCl_2$ | 89 |
| $CuCl_2$ | 100 |
| $ZnCl_2$ | 98 |
| $HgCl_2$ | 14 |
| $AgNO_3$ | 98 |
| $SnCl_2$ | 94 |
| $CdCl_2$ | 91 |

9. Molecular Weight

About 98,000 (measured by SDS-PAGE).

10. Influence of Ca

As a result of activity measurement on 1% pullulan containing 5 mM $CaCl_2$, no influence on the activity was observed. When the enzyme having an activity of 14 u/ml was treated with 5 mM $CaCl_2$ in a 50 mM acetic acid buffer solution (pH=5.0) for 30 minutes, no influence on temperature stability was observed.

11. Isoelectric Point

About 2.9.

The debranching enzyme according to the present invention is distinctly different from commercially available debranching enzymes, Promozyme (produced by Novo Nordisk A/S, hereinafter referred to as Enzyme A) and DB-250 (produced by Amano Pharmaceutical Co., Ltd., hereinafter referred to as Enzyme B), as shown in Table 5 below.

TABLE 5

| Item | Enzyme of Invention | Enzyme A | Enzyme B |
|---|---|---|---|
| Enzyme-producing Strain | Bacillus Sp. APC-9603 | Bacillus acidopullulyticus | Bacillus sectorramus |
| Relative Activity on Substrate: | | | |
| Pullulan | 100 | 100 | 100 |
| Soluble Starch (Merck) | 32.6 | 18.0 | 19.2 |
| Soluble Starch (Katayama) | 35.4 | 18.1 | 19.4 |
| Amylopectin (corn) | 48.1 | 19.6 | 18.1 |
| Amylopectin (potato) | 41.0 | 25.5 | 27.8 |
| Soluble Amylopectin (corn) | 62.9 | 34.5 | 26.0 |

TABLE 5-continued

| Item | Enzyme of Invention | Enzyme A | Enzyme B |
|---|---|---|---|
| Glycogen (oyster) | 16.7 | 7.6 | 3.8 |
| Optimum pH | ca. 5.2 | 3.5–5.5 | 5.0–5.5 |
| pH Stability | 4.0–6.0 | — | 4.5–6.5 |
| Optimum Temperature | around 65° C. | 60° C. | around 55° C. |
| Temperature Stability: | | | |
| 40° C. × 30 mins | — | — | 80% |
| 60° C. × 72 hrs | — | 50% | — |
| 70° C. × 30 mins | 80% | — | — |
| Influence of Inhibitor: | | | |
| EDTA | 90% | 129% | 93% |
| p-CMB | 81% | 14% | 27% |
| N-EMI | 104% | 69% | 66% |
| MIA | 105% | 68% | 67% |
| Influence of Metal Salt: | | | |
| $MgCl_2$ | 103% | 89% | 91% |
| $MnCl_2$ | 84% | 104% | 86% |
| $CoCl_2$ | 107% | 111% | 88% |
| $CaCl_2$ | 100% | 100% | 79% |
| $NiCl_2$ | 100% | 49% | 103% |
| $BaCl_2$ | 97% | 92% | 99% |
| $FeCl_3$ | 89% | 1% | 58% |
| $CuCl_2$ | 100% | 0% | 73% |
| $ZnCl_2$ | 98% | 96% | 97% |
| $HgCl_2$ | 14% | 28% | 0% |
| $AgNO_3$ | 98% | 16% | 3% |
| $SnCl_2$ | 94% | 110% | 82% |
| $CdCl_2$ | 91% | 25% | 92% |
| Molecular Weight (SDS-PAGE) | 98,000 | 100,000 | 95,500 |
| Isoelectric Point | c.a. 2.9 | c.a. 5.6 | ca. 4.7 |

The differences between the debranching enzyme of the present invention and known debranching Enzymes A and B are summarized below.

1. The enzyme of the invention is produced from Bacillus sp. APC-9603, while Enzymes A and B are produced from B. acidopullulyticus and B. sectorramus, respectively.
2. The enzyme of the invention acts on not only pullulan but also relatively long chain saccharides (e.g., soluble starch, amylopectin, glycogen, etc.), whereas both Enzymes A and B exhibit very high specificity on pullulan.
3. The optimum temperature of the enzyme of the invention, Enzyme A, and Enzyme B is 65° C., 60° C., and 55° C., respectively.
4. The enzyme of the invention exhibits 80% stability when treated at 70° C. for 30 minutes.
5. The enzyme of the invention is relatively less susceptible to various inhibitors, whereas Enzyme A and Enzyme B are inhibited by p-CMB to a large extent.
6. The enzyme of the invention is not influenced by various metal salts other than $Hg^{2+}$, whereas Enzyme A is inhibited by $Ni^{2+}$, $Fe^{3+}$, $Cu^{2+}$, $Hg^{2+}$, $Ag^{2+}$, and $Cd^{2+}$ to a considerable extent, and Enzyme B is inhibited by $Fe^{3+}$, $Hg^{2+}$, and $Ag^{2+}$ to a considerable extent.
7. The isoelectric point of the enzyme of the invention, Enzyme A, and Enzyme B is about 2.9, about 5.6, and about 4.7, respectively.

As described above, the debranching enzyme of the present invention exhibits entirely different enzymological and chemical properties from those of Enzymes A and B. In particular, the heat resistance of the enzyme of the invention is higher than that of the known debranching enzymes. Further, the enzyme of the invention has quite different substrate specificity from that of not only Enzyme A or Enzyme B but all of the reported α-1,6-glucosidases.

In other words, the α-1,6-glucosidase classified into EC 3.2.1.68, i.e., pullulanase, is very specific to pullulan while having a weak activity on amylopectin or soluble starch and a further weaker activity on glycogen. The α-1,6-glucosidase classified into EC 3.2.1.41, i.e., isoamylase, is active on amylopectin, soluble starch and glycogen but is substantially inactive on pullulan.

To the contrary, the debranching enzyme according to the present invention broadly acts on not only pullulan but amylopectin, soluble starch and glycogen. It has broader substrate specificity as compared with known debranching enzymes. That is, it is active also on α-1,6 bonds of relatively long-chain saccharides, thus achieving excellent reaction efficiency. Accordingly, the enzyme of the present invention is deemed to be a newly discovered debranching enzyme.

The debranching enzyme of the present invention is useful as an additive for increasing yield in production of glucose from starch by the action of a glucoamylase or as an enzyme for production of maltose in high yield from starch in combination with β-amylase.

Glucose has been produced by liquefying starch with an α-amylase and then saccharifying the product to glucose using a glucoamylase. Increase in the yield as high as possible has been desired. Since an increase in yield may be achieved by positively cleaving the α-1,6-glycoside bond which constitutes the branched structure, a so-called debranching enzyme has been used in combination. In this connection, substrate specificity of the conventional debranching enzymes is limited to saccharides of relatively short chain. Thus, use of an enzyme which exerts its debranching activity on not only short-chain saccharides but long-chain saccharides with α-1,6 bonds which are produced in the initial stage of the glucose production will improve the saccharification yield and reduce saccharification time.

The above-described advantage of the enzyme of the present invention also can be used in maltose production.

Saccharification of starch is usually carried out at a temperature of from 55° to 65° C., and preferably 60° C., and at a pH of from 4.0 to 5.0, and preferably from 4.3 to 4.7.

While the conditions will vary somewhat depending on the saccharification conditions, glucoamylase, β-amylase, and the debranching enzyme of the present invention are usually used in an amount of from 2 to 4 units, from 2 to 5 units, and from 0.05 to 0.5 units, respectively.

The present invention is now illustrated in greater detail by reference to the following Examples, but it should be understood that the present invention is not to be construed as being limited thereto. Unless otherwise indicated herein, all parts, percents, ratios and the like are by weight.

In the Examples, measurements of enzyme activity were made as follows.

To 0.5 ml of a 1% pullulan solution in a 100 mM McIlvaine's buffer solution (pH=5.0) was added 0.5 ml of an enzyme solution, and the system was allowed to react at 50° C. for 30 minutes. The reducing power thus produced was quantitatively determined through a 3,5-dinitrosalicylic acid reaction (the DNS method; cf. Borel et al., Helv. Chim. Acta., 35, 115 (1952)). The activity producing reducing power corresponding to 1 μmol of maltotriose for 1 minute was taken as one unit.

EXAMPLE 1

A medium containing 1.5% soluble starch, 0.5% polypeptone, 0.25% yeast extract, 0.1% ammonium sulfate, 0.1% potassium secondary phosphate, and 0.25% magnesium sulfate (pH=5.0) was inoculated with Bacillus sp. APC-9603 and shake-culturing was conducted in a Sakaguchi's flask at 37° C. for 72 hours to obtain a culture having a pullulanase activity of 0.9 u/ml. The culture (9 l) was centrifuged to remove microbial cells, and the supernatant liquor was concentrated using ultrafiltration. The concentrate was salted out with 90% saturated ammonium sulfate, followed by centrifugal separation. The precipitate collected was dissolved in a 5 mM acetic acid buffer solution (pH=5.0) and subjected to dialysis against the same buffer solution. The dialysate was concentrated through a membrane "Amicon Diaflo Membrane PM-10" (commercially available from Amicon corporation) to 130 ml.

The concentrate was applied to a column of "DEAE-Sepharose CL-6B" (commercially available from Pharmacia Co.) equilibrated with a 10 mM phosphate buffer solution (pH=7.0) and eluted with a sodium chloride solution at a linear gradient of from 0 to 0.5M. The eluate was dialyzed against a 50 mM acetic acid buffer solution (pH=5.0), adsorbed on $\gamma$-cyclodextrin-Sepharose 6B which was prepared using "Sepharose 6B" (a product of Pharmacia Co.) (cf. FEBS Letters 47(1), 86 (1974)), and eluted with 0.6% $\gamma$-cyclodextrin. The eluate was concentrated through "Amicon Diaflo Membrane PM-10", subjected to gel filtration using a column of "Toyo Pearl HW-55S" (a product of Toso Co.) equilibrated with a 50 mM acetic acid buffer solution (pH=5.0) containing 0.5M sodium chloride to obtain a purified enzyme showing a single band in SDS-PAGE analysis.

EXAMPLE 2

A medium containing 1.0% maltose, 0.5% polypeptone, 0.25% yeast extract, 0.2% potassium secondary phosphate, and 0.1% magnesium sulfate (pH=5.0) was placed in a 30 l-volume jar fermentor and inoculated with Bacillus sp. APC-9603, followed by spinner culture with aeration at 37° C. for 48 hours. The resulting culture had a pullulanase activity of 0.5 u/ml. The microbial cells were separated by centrifugation, and the supernatant liquor was about 100-fold concentrated through an ultrafilter to obtain a crude enzyme liquid preparation with a pullulanase activity of 38 u/ml (pH=5.0). The crude enzyme was subjected to ammonium sulfate fractionation and then affinity chromatography using a column of $\gamma$-Cyclodextrin-Sepharose 6B which was prepared using "Sepharose 6B" (a product of Pharmacia Co.) (cf. FEBS Letters 47(1), 86 (1974)) to obtain a purified enzyme having a specific activity of 225 u/mg-protein.

EXAMPLE 3

A medium containing 2.0% waxy starch, 2.0% of meat extract, 0.2% potassium secondary phosphate, and 0.1% magnesium sulfate (pH=5.0) was placed in a 1000 l-volume tank and inoculated with Bacillus sp. APC-9603, followed by spinner culture with aeration at 37° C. for 48 hours. The culture had a pullulanase activity of 0.4 u/ml. The resulting culture was treated in the same manner as in Example 2 to obtain about 1 l of a crude enzyme liquid preparation of the debranching enzyme having an activity of about 150 u/ml.

EXAMPLE 4

Saccharification was performed under the following conditions.

Substrate: Liquefied starch (DE(Dextrose equivalent) 11, 30% (w/w))
Enzyme: "Gluczyme NL-3" produced by Amano Pharmaceutical Co., Ltd. (2.5 u/g-DS) The debranching enzyme obtained in Example 3 (0.25 to 0.400 u/g-DS)

Reaction Conditions

Temp.: 60° C.
pH: 4.5
Time: 16, 24 or 40 hrs.

The resulting saccharification mixture was analyzed using high performance liquid chromatography to determine the content of monosaccharides (G1), disaccharides (G2), trisaccharides (G3), and polysaccharides (Gn). As a control, saccharification was conducted in the same manner but without using any debranching enzyme of the present invention. The results obtained are shown in Table 6 below.

REFERENCE EXAMPLE 1

Saccharification was performed in the same manner as in Example 4, except the debranching enzyme of the present invention was replaced with Promosyme (A). The results of analysis are also shown in Table 6 below.

TABLE 6

| Reaction Time (hr) | Debranching Enzyme | Saccharides | Amount of Debranching Enzyme Added ($\mu$/g-DS) | | | |
|---|---|---|---|---|---|---|
| | | | 0 | 0.25 | 0.1 | 0.4 |
| 16 | Invention | G1 | 87.32% | 88.47% | 90.64% | 93.40% |
| | | G2 | 1.95 | 2.10 | 2.34 | 2.52 |
| | | G3 | 0.53 | 0.63 | 0.84 | 1.04 |
| | | Gn | 10.20 | 8.80 | 6.18 | 3.04 |
| 16 | A | G1 | — | 87.68 | 88.99 | 90.34 |
| | | G2 | — | 1.97 | 2.14 | 2.42 |
| | | G3 | — | 0.55 | 0.69 | 0.81 |
| | | Gn | — | 9.80 | 8.18 | 6.43 |
| 24 | Invention | G1 | 91.64 | 93.17 | 94.92 | 96.14 |
| | | G2 | 1.89 | 2.03 | 2.08 | 1.92 |
| | | G3 | 0.46 | 0.65 | 0.77 | 0.82 |
| | | Gn | 6.01 | 4.15 | 2.23 | 1.12 |
| 24 | A | G1 | — | 91.97% | 93.38% | 94.61% |
| | | G2 | — | 1.93 | 2.02 | 2.05 |
| | | G3 | — | 0.54 | 0.67 | 0.74 |
| | | Gn | — | 5.56 | 3.93 | 2.60 |
| 40 | Invention | G1 | 94.29% | 95.59 | 96.10 | 96.48 |

TABLE 6-continued

| Reaction Time (hr) | Debranching Enzyme | Saccharides | Amount of Debranching Enzyme Added (μ/g-DS) | | | |
|---|---|---|---|---|---|---|
| | | | 0 | 0.25 | 0.1 | 0.4 |
| | | G2 | 2.17 | 2.24 | 2.23 | 2.20 |
| | | G3 | 0.39 | 0.57 | 0.58 | 0.58 |
| | | Gn | 3.15 | 1.60 | 1.09 | 0.74 |
| 40 | A | G1 | — | 94.59 | 95.46 | 96.09 |
| | | G2 | — | 2.19 | 2.26 | 2.19 |
| | | G3 | — | 1.46 | 0.55 | 0.57 |
| | | Gn | — | 2.76 | 1.73 | 1.15 |

EXAMPLE 5

Saccharification was performed under the following conditions.

Substrate: Liquefied starch (DE(Dextrose equivalent) 4.6, 25% (w/w))

Enzyme: "Biozyme M5" produced by Amano Pharmaceutical Co., Ltd. (4.0 u/g-DS) The debranching enzyme obtained in Example 3 (0.25 to 1.00 u/g-DS)

Reaction Conditions

Temp.: 63° C.
pH: 5.5
Time: 24, 40, or 68 hrs.

The resulting saccharification mixture was analyzed in the same manner as in Example 4. As a control, saccharification was conducted in the same manner but without using any debranching enzyme of the present invention. The results obtained are shown in Table 7 below.

REFERENCE EXAMPLE 2

Saccharification was performed in the same manner as in Example 5, except the debranching enzyme of the present invention was replaced with Promozyme (A). The analysis results are shown in Table 7 below.

TABLE 7

| Reaction Time (hr) | Debranching Enzyme | Saccharides | Amount of Debranching Enzyme Added (μ/g-DS) | | | |
|---|---|---|---|---|---|---|
| | | | 0 | 0.25 | 0.50 | 1.00 |
| 24 | Invention | G1 | 0.0% | 0.0% | 0.1% | 0.1% |
| | | G2 | 58.5 | 69.7 | 74.2 | 76.5 |
| | | G3 | 9.5 | 12.4 | 13.4 | 13.9 |
| | | Gn | 32.2 | 17.9 | 12.3 | 9.5 |
| 24 | A | G1 | — | 0.1 | 0.1 | 0.2 |
| | | G2 | — | 64.6 | 67.3 | 69.2 |
| | | G3 | — | 11.4 | 12.1 | 12.6 |
| | | Gn | — | 23.9 | 20.5 | 18.0 |
| 40 | Invention | G1 | 0.0 | 0.0 | 0.0 | 0.0 |
| | | G2 | 59.0 | 73.0 | 76.5 | 79.0 |
| | | G3 | 9.6 | 13.1 | 13.9 | 14.4 |
| | | Gn | 31.4 | 13.9 | 9.6 | 6.6 |
| 40 | A | G1 | — | 0.1% | 0.0% | 0.2% |
| | | G2 | — | 66.7 | 70.5 | 72.4 |
| | | G3 | — | 11.9 | 12.7 | 13.2 |
| | | Gn | — | 21.3 | 16.8 | 14.2 |
| 48 | Invention | G1 | 0.0% | 0.0 | 0.0 | 0.0 |
| | | G2 | 59.3 | 74.8 | 78.4 | 78.9 |
| | | G3 | 9.5 | 13.4 | 14.1 | 14.3 |
| | | Gn | 31.2 | 11.8 | 7.7 | 6.8 |
| 48 | A | G1 | — | 0.1 | 0.1 | 0.2 |
| | | G2 | — | 67.5 | 70.8 | 73.5 |
| | | G3 | — | 12.1 | 12.9 | 13.4 |
| | | Gn | — | 20.3 | 16.2 | 12.9 |

As described and demonstrated above, the present invention provides a novel debranching enzyme exhibiting both isoamylase-like activity and pullulanase-like activity, a new strain Bacillus sp. APC-9603 capable of producing the debranching enzyme, a process for producing the enzyme, and a process of saccharification using the enzyme, thus making a great contribution to the starch saccharification field.

While the invention has been described in detail and with reference to specific examples thereof, it will be apparent to one skilled in the art that various changes and modifications can be made therein without departing from the spirit and scope thereof.

What is claimed is:

1. A substantially pure heat-stable debranching enzyme isolated from a Bacillus microorganism having the following properties:

1) Activity: Acts on α1,6-glucoside bonds to produce straight chain amylose,
2) Substrate Specificity: Acts on pullulan and also acts on relatively long chain saccharides, wherein when said substrate specificity for activity on pullulan is set at 100, the activity of said enzyme on soluble starches relative to said activity on pullulan is from about 20 to 40, the activity of said enzyme on glycogen relative to said activity on pullulan is from about 30 to 60, and the activity of said enzyme on amylopectin relative to said activity on pullulan is from about 10 to 30,
3) Optimum pH: from about 4.5 to about 6.0,
4) Optimum temperature: from about 60° C. to about 70° C.,
5) Molecular Weight: about 98 KD as measured by SDS-PAGE, and
6) Isoelectric point: about 2.9.

2. The substantially pure heat-stable debranching enzyme of claim 1, wherein said enzyme is isolated from Bacillus FERM BP-4204.

* * * * *

UNITED STATES PATENT AND TRADEMARK OFFICE
CERTIFICATE OF CORRECTION

PATENT NO. : 5,387,516
DATED : February 7, 1995
INVENTOR(S) : Michiyo KAWAI, Shigeharu MORI, SusumU HIROSE and Hiroji TSUJI It is certified that error appears in the above-identified patent and that said Letters Patent is hereby corrected as shown below:

Column 5, line 23, delete "Glycogens" and insert --Amylopectins--; and
line 24, delete "Amylopectins" and insert --Glycogens--.

Column 12, line 32, delete "glycogen" and insert --amylopectin--; and
line 34, delete "amylopectin" and insert --glycogen--.

Signed and Sealed this

Ninth Day of May, 2000

Attest:

Q. TODD DICKINSON

*Attesting Officer*     *Director of Patents and Trademarks*